(12) United States Patent
Durrant et al.

(10) Patent No.: US 11,595,478 B2
(45) Date of Patent: Feb. 28, 2023

(54) MEDICAL DEVICE MANAGEMENT

(71) Applicant: ZOLL Medical Corporation, Chelmsford, MA (US)

(72) Inventors: Ian B Durrant, Arlington, MA (US); C. Shane Reid, Denver, CO (US); Andrew D Funk, Boulder, CO (US); Patrick Shortall, Denver, CO (US)

(73) Assignee: ZOLL Medical Corporation, Chelmsford, MA (US)

( * ) Notice: Subject to any disclaimer, the term of this patent is extended or adjusted under 35 U.S.C. 154(b) by 409 days.

(21) Appl. No.: 16/507,415

(22) Filed: Jul. 10, 2019

(65) Prior Publication Data
US 2019/0349435 A1     Nov. 14, 2019

Related U.S. Application Data

(63) Continuation of application No. 15/084,270, filed on Mar. 29, 2016, now Pat. No. 10,924,553.
(Continued)

(51) Int. Cl.
*H04L 67/125*     (2022.01)
*G16H 40/40*     (2018.01)
(Continued)

(52) U.S. Cl.
CPC .............. *H04L 67/125* (2013.01); *G06F 8/65* (2013.01); *G06F 9/452* (2018.02); *G16H 40/40* (2018.01);
(Continued)

(58) Field of Classification Search
CPC ................................ H04L 41/20; H04L 41/08
See application file for complete search history.

(56) References Cited

U.S. PATENT DOCUMENTS 6,083,248 A    7/2000   Thompson
6,088,616 A    7/2000   Olson et al.
(Continued)

FOREIGN PATENT DOCUMENTS

WO    20070058835    5/2007
WO    20070089225    8/2007
(Continued)

OTHER PUBLICATIONS

International Search Report and Written Opinion issued by the U.S Patent and Trademark Office as International Searching Authority for International Application No. PCT/US13/43274, dated Aug. 30, 2013 (7 pages).
(Continued)

*Primary Examiner* — Nicholas R Taylor
*Assistant Examiner* — Sm Z Islam
(74) *Attorney, Agent, or Firm* — Zoll Medical Corporation

(57) ABSTRACT

A medical device for use in patient resuscitation and that is configured to communicate with one or more management servers includes a memory, a processor communicably coupled to the memory and configured to store device status information including device-readiness information from a medical device self-test, and store clinical event information observed by the medical device during a use of the medical device during a clinical event, the clinical event information including CPR performance data, and a communication component communicably coupled to the processor and configured to wirelessly transmit the device status information and the clinical event information to the one or more management servers, wherein the medical device includes an external defibrillator, an automated external defibrillator, or a compression assistance device.

26 Claims, 5 Drawing Sheets

Related U.S. Application Data

(60) Provisional application No. 62/140,398, filed on Mar. 30, 2015.

(51) Int. Cl.

| | | |
|---|---|---|
| *G06F 9/451* | (2018.01) | |
| *G16H 40/67* | (2018.01) | |
| *G06F 8/65* | (2018.01) | |
| *H04L 5/14* | (2006.01) | |
| *H04L 41/08* | (2022.01) | |
| *H04L 41/00* | (2022.01) | |
| *H04L 41/22* | (2022.01) | |
| *H04L 43/16* | (2022.01) | |
| *H04L 67/00* | (2022.01) | |
| *H04W 84/12* | (2009.01) | |
| *H02J 7/00* | (2006.01) | |

(52) U.S. Cl.
CPC ............... *G16H 40/67* (2018.01); *H04L 5/14* (2013.01); *H04L 41/08* (2013.01); *H04L 41/20* (2013.01); *H04L 41/22* (2013.01); *H04L 43/16* (2013.01); *H04L 67/34* (2013.01); *H04W 84/12* (2013.01); *H02J 7/0048* (2020.01)

(56) References Cited

U.S. PATENT DOCUMENTS

| | | | |
|---|---|---|---|
| 6,363,282 B1 | 3/2002 | Nichols et al. | |
| 6,370,428 B1 | 4/2002 | Snyder et al. | |
| 6,397,104 B1 | 5/2002 | Miller et al. | |
| 6,492,581 B1 | 12/2002 | Bradbury | |
| 6,747,556 B2 | 6/2004 | Medema et al. | |
| 6,754,526 B2 | 6/2004 | Daynes et al. | |
| 6,813,517 B2 | 11/2004 | Daynes et al. | |
| 6,937,150 B2 | 8/2005 | Medema et al. | |
| 7,220,235 B2 * | 5/2007 | Geheb .................... G16H 40/63 | |
| | | | 600/587 |
| 7,672,720 B2 | 3/2010 | Heath | |
| 7,769,465 B2 | 8/2010 | Matos | |
| 7,805,190 B2 | 9/2010 | Chapman et al. | |
| 7,937,146 B2 | 5/2011 | Banville et al. | |
| 7,979,378 B2 | 7/2011 | West et al. | |
| 8,081,071 B1 | 12/2011 | Vaisnys et al. | |
| 8,781,577 B2 | 7/2014 | Freeman | |
| 8,880,166 B2 | 11/2014 | Tan et al. | |
| 9,119,971 B2 | 9/2015 | Elghazzawi | |
| 9,220,912 B2 | 12/2015 | Elghazzawi | |
| 9,224,171 B2 | 12/2015 | Peak et al. | |
| 2001/0016696 A1 | 8/2001 | Bystrom et al. | |
| 2003/0025602 A1 | 2/2003 | Medema et al. | |
| 2003/0028219 A1 | 2/2003 | Powers et al. | |
| 2003/0212311 A1 | 11/2003 | Nova et al. | |
| 2003/0212438 A1 | 11/2003 | Nova et al. | |
| 2004/0049233 A1 | 3/2004 | Edwards | |
| 2004/0064342 A1 | 4/2004 | Browne et al. | |
| 2004/0214148 A1 | 10/2004 | Salvino et al. | |
| 2005/0015115 A1 | 1/2005 | Sullivan et al. | |
| 2006/0030891 A1 | 2/2006 | Saltzstein et al. | |
| 2006/0083785 A1 | 4/2006 | Kerrish et al. | |
| 2006/0084043 A1 | 4/2006 | Weaver et al. | |
| 2006/0149321 A1 | 7/2006 | Merry et al. | |
| 2007/0032830 A1 | 2/2007 | Bowers | |
| 2007/0108274 A1 | 5/2007 | Boardman et al. | |
| 2007/0185545 A1 | 8/2007 | Duke | |
| 2008/0138778 A1 | 6/2008 | Eggert et al. | |
| 2008/0215360 A1 | 9/2008 | Dicks et al. | |
| 2009/0157695 A1 * | 6/2009 | Roberts .................. G16H 40/67 | |
| 2009/0222539 A1 | 9/2009 | Lewis et al. | |
| 2009/0275354 A1 * | 11/2009 | Bulmer .................. G06F 1/3203 | |
| | | | 455/522 |
| 2010/0063559 A1 | 3/2010 | McIntyre et al. | |
| 2010/0250643 A1 | 9/2010 | Savage et al. | |
| 2011/0057082 A1 | 3/2011 | West | |
| 2011/0060378 A1 * | 3/2011 | Tuysserkani ......... A61B 5/0022 | |
| | | | 370/352 |
| 2011/0284004 A1 | 11/2011 | Silver et al. | |
| 2011/0295078 A1 | 12/2011 | Reid et al. | |
| 2012/0081230 A1 * | 4/2012 | Sullivan .................... G08B 3/10 | |
| | | | 340/636.1 |
| 2012/0197196 A1 * | 8/2012 | Halbert ................... G16Z 99/00 | |
| | | | 604/151 |
| 2013/0132465 A1 | 5/2013 | Brown | |
| 2013/0312066 A1 | 11/2013 | Suarez et al. | |
| 2013/0346108 A1 * | 12/2013 | Kamen .................. G16H 40/67 | |
| | | | 705/2 |
| 2015/0105701 A1 | 4/2015 | Mayer et al. | |
| 2015/0224021 A1 * | 8/2015 | Centen ................. A61H 31/005 | |
| | | | 601/41 |
| 2015/0321020 A1 * | 11/2015 | Gumbrell ............. A61N 1/3925 | |
| | | | 607/5 |

FOREIGN PATENT DOCUMENTS

| | | |
|---|---|---|
| WO | 20090136259 | 11/2009 |
| WO | 20140033605 | 3/2014 |

OTHER PUBLICATIONS

International Search Report and Written Opinion issued by the U.S. Patent and Trademark Office as International Searching Authority for International Application No. PCT/US16/24790 dated Jun. 30, 2016 (13 pages).

Supplementary European Search Report for Application No. 16774019.0 dated Jul. 12, 2018 (15 pages).

Notice of Reasons for Rejection for JP Application No. 2017-550196 with English translation, dated Jan. 14, 2020, 7 pages.

\* cited by examiner

MEDICAL DEVICE MANAGEMENT

CROSS-REFERENCE TO RELATED APPLICATIONS

This application is a continuation under 35 U.S.C. § 120 of U.S. patent application Ser. No. 15/084,270, filed on Mar. 29, 2016 and issued as U.S. Pat. No. 10,924,553, which claims the benefit of U.S. Provisional Patent Application Ser. No. 62/140,398, filed on Mar. 30, 2015. All subject matter set forth in each of the above referenced application is hereby incorporated by reference in its entirety into the present application as if fully set forth herein.

TECHNICAL FIELD

Embodiments of the present disclosure relate generally to monitoring and managing medical devices.

BACKGROUND

Medical devices configured for infrequent use in medical situations (for example, emergent situations) often are disposed at non-medical facilities, are powered by batteries, and may sometimes rely on patient-interface components such as electrodes that have a limited useful life. Conventional devices such as, for example, automated external defibrillators (AEDs) may employ automated self-tests to ensure that the device will work when it is needed. However, these devices typically store the results of the self-tests in a local memory and, therefore, self-test failures often go unrecognized. For example, defibrillator failure may be detected when a caregiver attempts to use it to save a life. Additionally, caregivers benefit from the sharing of clinical event information when care of a patient is being transitioned.

SUMMARY

A system for remotely managing a medical device according to an embodiment of the present disclosure includes a medical device that is disposed at a first location, wherein the medical device is configured for infrequent use in medical situations, the medical device comprising a first communication component configured to facilitate transmitting information through a network; and a server device disposed at a second location and communicatively coupled to the network, the server device comprising a memory and a processor communicably coupled to the memory, the memory including instructions that, when executed by the processor, cause the processor to initiate at least one component, the at least one component comprising: a second communication component configured to receive the information, the information comprising device readiness information; and a graphical user interface (GUI) component configured to facilitate presentation of a representation of the information to a user; the first communication component further configured to facilitate transmitting the information through the network automatically and without a request from the server device. In one embodiment of the present disclosure, the memory is a first memory, the medical device comprising a second memory, the second memory comprising a schedule, wherein the first communication component is further configured to facilitate transmitting the information through the network automatically and without a request from the server device according to the schedule. In another embodiment of the present disclosure, the first communication component is further configured to facilitate transmitting the information through the network automatically and without a request from the server device upon occurrence of an event or condition. In such cases, the event or condition may be one or a combination of events or conditions selected from the group including: power down of the medical device, docking of the medical device, passage of a period of time, passage of a period of time since the information was transmitted through the network, conclusion of a medical event for which the medical device was used, battery level falling below a threshold, and occurrence of a device readiness fault.

The system as described above, wherein the second communication component facilitates bidirectional communication with the first communication component.

The system as described above, wherein the medical device is powered by a battery and wherein the device-readiness information comprises information associated with a remaining life of the battery.

The system as described above, wherein the device-readiness information comprises information associated with a remaining life of at least one patient-interface component of the medical device.

The system as described above, wherein the at least one patient-interface component comprises at least one defibrillation electrode.

The system as described above, wherein the medical device comprises an automated external defibrillator (AED).

The system as described above, further comprising an additional medical device, and wherein the additional medical device includes the server device.

The system as described above, wherein the additional medical device comprises an automated external defibrillator (AED).

The system as described above, wherein the medical device is configured for use in emergent situations.

The system as described above, wherein the network comprises a wireless local area network (WLAN).

The system as described above, wherein the WLAN comprises a WiFi network.

The system as described above, wherein the server device is further configured to provide at least one of a configuration file and a software update to the medical device.

The system as described above, further comprising an additional server device, the additional server device configured to (1) receive the information from the medical device, and (2) provide the information to the server device.

A system for remotely managing a medical device according to an embodiment of the present disclosure includes a medical device that is disposed at a first location, wherein the medical device is configured for infrequent use in medical situations, the medical device comprising a first communication component configured to facilitate transmitting information through a network; and a server device disposed at a second location and communicatively coupled to the network, the server device comprising a memory and a processor communicably coupled to the memory, the memory including instructions that, when executed by the processor, cause the processor to initiate at least one component, the at least one component comprising: a second communication component configured to receive the information, the information comprising device performance information; and a graphical user interface (GUI) component configured to facilitate presentation of a representation of the information to a user, the first communication component further configured to facilitate transmitting the information through the network automatically and without a request from the server device. In one embodiment of the present disclosure, the memory is a first memory, the medical device comprising a second memory, the second memory comprising a schedule, wherein the first communication component is further configured to facilitate transmitting the information through the network automatically and without a request from the server device according to the schedule. In another embodiment of the present disclosure, the first communication component is further configured to facilitate transmitting the information through the network automatically and without a request from the server device upon occurrence of an event or condition. In such cases, the event or condition may be one or a combination of events or conditions selected from the group including: power down of the medical device, docking of the medical device, passage of a period of time, passage of a period of time since the information was transmitted through the network, conclusion of a medical event for which the medical device was used, battery level falling below a threshold, and occurrence of a device readiness fault.

The system as described above, wherein the second communication component facilitates bidirectional communication with the first communication component.

The system as described above, wherein the medical device is powered by a battery and wherein the device-readiness information comprises information associated with a remaining life of the battery.

The system as described above, wherein the device-readiness information comprises information associated with a remaining life of at least one patient-interface component of the medical device.

The system as described above, wherein the at least one patient-interface component comprises at least one defibrillation electrode.

The system as described above, wherein the medical device comprises an automated external defibrillator (AED).

The system as described above, further comprising an additional medical device, and wherein the additional medical device includes the server device.

The system as described above, wherein the additional medical device comprises an automated external defibrillator (AED).

The system as described above, wherein the medical device is configured for use in emergent situations.

The system as described above, wherein the network comprises a wireless local area network (WLAN).

The system as described above, wherein the WLAN comprises a WiFi network.

The system as described above, wherein the server device is further configured to provide at least one of a configuration file and a software update to the medical device.

The system as described above, further comprising an additional server device, the additional server device configured to (1) receive the information from the medical device, and (2) provide the information to the server device.

A system according to an embodiment of the present disclosure for remotely managing a medical device that is configured for infrequent use in medical situations, the medical device in a first location, the system includes a memory; and a processor communicably coupled to the memory, the memory including instructions that, when executed by the processor, cause the processor to initiate at least one component, the at least one component comprising: a communication component configured to receive information from the medical device while the medical device is not in therapy mode, the information comprising clinical event information recorded while the medical device was in therapy mode; and a graphical user interface (GUI) component configured to facilitate presentation of a representation of the information to a user in a second location.

The system as described above, wherein the medical device is an automatic external defibrillator (AED).

The system as described above, wherein the communication component is further configured to receive the information from the AED automatically and without requesting the information from the AED.

The system as described above, wherein the clinical event information comprises at least one physiological parameter associated with a patient, recorded during a clinical event in which the AED was used on the patient.

A system for remotely managing a medical device disposed at a first location according to an embodiment of the present disclosure, wherein the medical device is configured for infrequent use in medical situations, includes a server device communicatively coupled to a network, the server device comprising a memory and a processor communicably coupled to the memory, the memory including instructions that, when executed by the processor, cause the processor to initiate at least one component, the at least one component comprising: a communication component configured to facilitate bidirectional communication with the medical device; a configuration component configured to facilitate remote configuration of the medical device, the configuration component further configured to receive a message from the medical device indicating one or more of a device type and a current software version and to automatically configure the medical device based on the indication; and a graphical user interface (GUI) configured to facilitate interaction between a user at a second location and at least one of the configuration component and the communication component.

The system as described above, wherein the at least one component further comprises an update component configured to facilitate remote management of software running on the medical device.

The system as described above, wherein the communication component is further configured to receive information from the medical device, the information comprising two or more of clinical event information, device performance information, and device-readiness information.

The system as described above, wherein the information comprises clinical event information, device performance information, and device-readiness information.

The system as described above, wherein the device-readiness information comprises information associated with a remaining life of at least one of a battery and at least one patient-interface component of the medical device.

The system as described above, wherein the at least one patient-interface component comprises a defibrillation electrode.

The system as described above, wherein the medical device comprises an automated external defibrillator (AED).

A system for remotely managing a medical device that is disposed at a first location according to an embodiment of the present disclosure, wherein the medical device is configured for infrequent use in medical situations, the system comprising: a memory; and a processor communicably coupled to the memory, the memory including instructions that, when executed by the processor, cause the processor to initiate at least one component, the at least one component comprising: a communication component configured to receive information from a medical device, the information comprising two or more of device-readiness information, device performance information, and clinical event information; and a graphical user interface (GUI) component configured to facilitate presentation of a representation of the information to a user.

The system as described above, wherein the communication component facilitates bidirectional communication with the medical device.

The system as described above, wherein the communication component facilitates automatic transmission of the information from the medical device.

The system as described above, wherein the medical device is powered by a battery and wherein the device-readiness information comprises information associated with a remaining life of the battery.

The system as described above, wherein the device-readiness information comprises information associated with a remaining life of at least one patient-interface component of the medical device.

The system as described above, wherein the at least one patient-interface component comprises at least one defibrillation electrode.

The system as described above, wherein the medical device comprises an automated external defibrillator (AED).

The system as described above, wherein the medical device is configured for use in emergent situations.

The system as described above, wherein the information comprises clinical event information, device performance information, and device-readiness information.

The system as described above, wherein the clinical event information comprises at least one physiological parameter associated with a patient, recorded during a clinical event in which the medical device was used.

The system as described above, the at least one component further comprising a configuration component configured to facilitate providing a configuration file to the medical device.

The system as described above, the at least one component further comprising an update component configured to facilitate providing a software update to the medical device.

An embodiment of the present disclosure includes one or more computer-readable media having computer-executable instructions embodied thereon that, when executed by a processor, cause the processor to initiate at least one program component, the at least one program component comprising: a communication component configured to receive information from a medical device, the information comprising two or more of clinical event information, device performance information, and device-readiness information; and a device dashboard configured to facilitate management of the information.

The media as described above, wherein the device-readiness information comprises information associated with a remaining life of at least one of a battery and at least one patient-interface component of the medical device.

The media as described above, wherein the at least one patient-interface component comprises a defibrillation electrode.

The media as described above, wherein the information comprises clinical event information, device performance information, and device-readiness information.

The media as described above, wherein the medical device comprises an automated external defibrillator (AED).

The media as described above, the at least one component further comprising a configuration component configured to facilitate providing a configuration file to the medical device.

The media as described above, the at least one component further comprising an update component configured to facilitate providing a software update to the medical device.

While multiple embodiments are disclosed, still other embodiments of the invention will become apparent to those skilled in the art from the following detailed description, which shows and describes illustrative embodiments. Accordingly, the drawings and detailed description are to be regarded as illustrative in nature and not restrictive.

Figure 1:
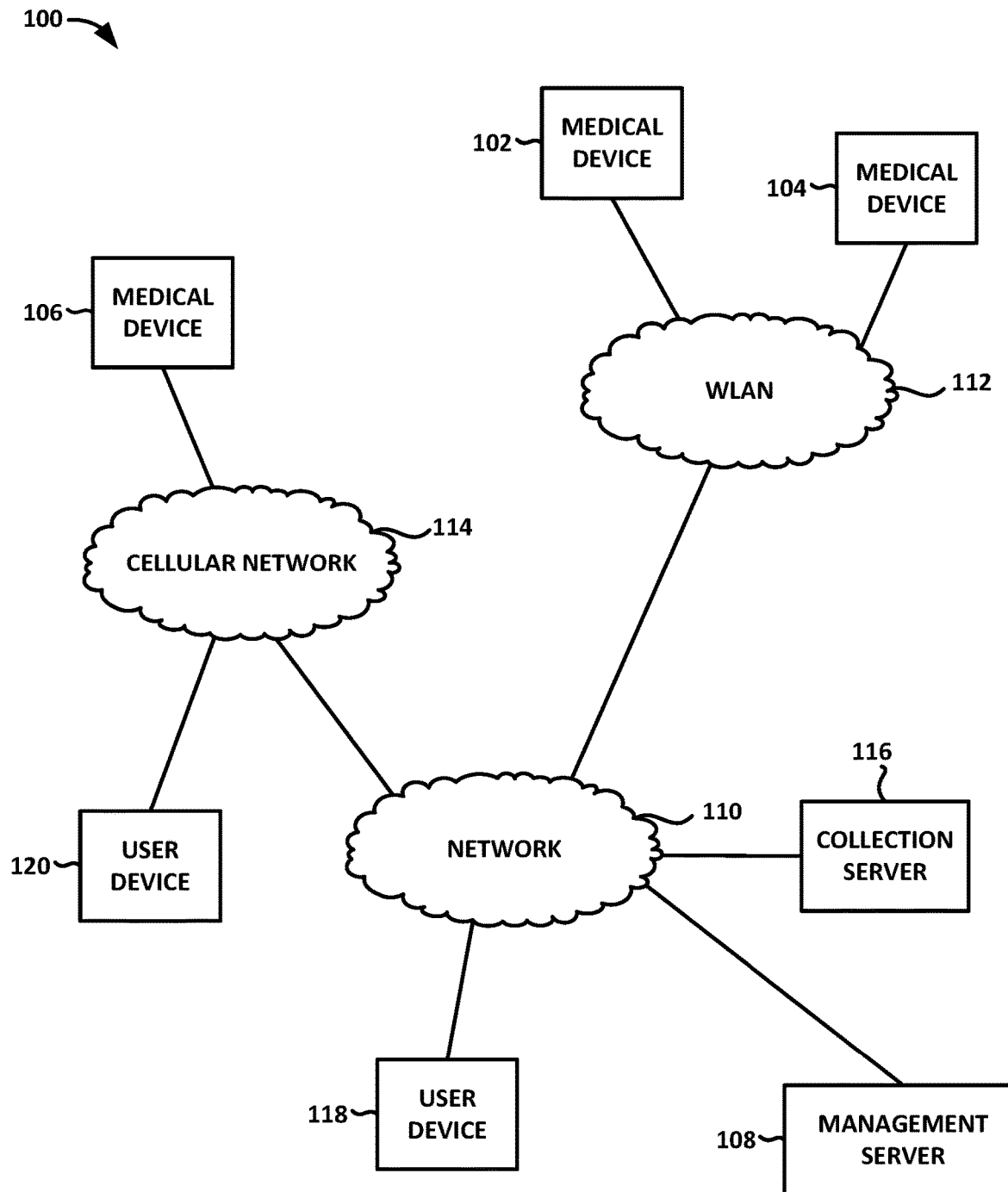
FIG. 1 depicts an illustrative operating environment in accordance with embodiments of the present disclosure.

While the present invention is amenable to various modifications and alternative forms, specific embodiments have been shown by way of example in the drawings and are described in detail below. The present invention, however, is not limited to the particular embodiments described. On the contrary, the present invention is intended to cover all modifications, equivalents, and alternatives falling within the ambit of the present invention as defined by the appended claims.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

Various types of facilities (for example, hospitals, schools, office buildings, airplanes, busses, etc.) may be equipped with one or more medical devices configured for infrequent use in medical situations. As used herein, the phrases "medical situations" and "medical events" are used in their broadest sense to refer to may include any situation or event in which medical attention is called for, in which a patient experiences a medical problem, or in which a patient has treatment or care, and includes, for example, emergent situations. For example, and without limitation, a medical event may begin when a patient experiences medical symptoms and a call is made to emergency services (e.g. emergency medical services), and the medical event may end when the patient has been evaluated, treated, transported, and/or released. A medical event or situation may include various events within the medical event, including for example emergency transport. Medical devices configured for infrequent use in medical situations include medical devices that are generally not used in a continuous manner, but are used less frequently. As the phrase is used herein, "infrequent use" may include intermittent use with some period of time between uses, several uses, one use, no uses, and/or the like. For example, automated external defibrillators (AEDs) are designed to be used in medical situations involving a victim of cardiac arrest, which is not an event that occurs frequently, if at all, in some locations. Thus, an AED may remain unused for several years before being used only once, if at all. In other situations, such a medical device may only be used occasionally.

Because these types of medical devices may not need to be used frequently, they often are placed in service and not maintained for long periods of time. When the medical devices are needed, however, users rely on them to function properly. Medical devices such as AEDs benefit from regular maintenance and/or monitoring for optimal functionality and performance. Embodiments of the invention facilitate remote monitoring of the condition of such medical devices. Additionally, following an event where a medical device is used, the responders or other clinicians often desire to view clinical event information generated during the use. Embodiments of the invention facilitate capturing and managing this type of information, as well.

According to embodiments, a medical device (for example, an AED) is configured to transmit self-test information, clinical event information, and/or the like to a server that is associated with a medical device management service, which may be, for example, web-based. The management service may be configured allow users to view, manipulate, convert, aggregate, analyze, and/or otherwise manage information received from medical devices, information about medical devices, software updates for medical devices, configuration updates for medical devices, clinical event information, and/or the like. In embodiments, the management service is configured to be incorporated into a user's daily activities and to conveniently facilitate adjusting medical device configuration, updating medical device software, updating and/or maintaining site compliance, viewing device-readiness and/or device performance, viewing clinical event information, viewing device locations in a geographical area, and/or the like.

FIG. 1 depicts an illustrative operating environment 100 (and, in some embodiments, aspects of the present invention) in accordance with embodiments of the present invention, as illustrated by way of example. As shown in FIG. 1, the illustrative operating environment 100 may include a number of medical devices 102, 104, and 106 that communicate with one or more management servers 108 via one or more networks 110. The network 110 may be, or include, any number of different types of communication networks such as, for example, a short messaging service (SMS), a local area network (LAN), a wireless LAN (WLAN), a wide area network (WAN), the Internet, a peer-to-peer (P2P) network, a direct wired connection between two or more devices (for example, an RS-232 connection), a direct wireless connection between two or more devices (for example, a Bluetooth® connection), and/or the like. In embodiments, the network 110 may be a combination of networks.

The medical devices 102, 104, and/or 106 may be configured for infrequent use in emergent or medical situations. For example, the medical devices 102, 104, and 106 may include, for example, an automated external defibrillator (AED), a portable infuser, and/or the like. The medical devices 102, 104, and/or 106 may be, for example, defibrillators (for example, ZOLL® X-Series®, E-Series®, or R-Series® devices), automatic external defibrillators (AEDs) (for example, ZOLL® AED Pro® devices, ZOLL® AED Plus® devices), wearable cardioverter defibrillators (for example, ZOLL® LifeVest® devices), portable electronic infusion pumps (for example, ZOLL® Power Infuser® devices), device systems (for example, ZOLL® Propaq® systems), compression assistance devices or technologies (for example, ZOLL® Real CPR Help®, ZOLL® AutoPulse®, or ZOLL® PocketCPR®), ventilation assistance devices (for example, IMPACT® Instrumentation ventilators) and/or the like. The medical devices 102, 104, and/or 106 may be configured to provide therapy (for example, defibrillation shocks, infused medicines, and/or the like), and/or to monitor, detect, and/or derive or calculate various physiological parameters such as, for example, heart rate, blood pressure, temperature, respiration rate, blood oxygen level, end-tidal carbon dioxide level, pulmonary function, blood glucose level, weight, and/or the like. In embodiments, the medical devices 102, 104, and/or 106 may determine and/or present waveforms such as, for example, electrocardiograms (ECGs).

In embodiments, the medical devices 102, 104, and/or 106 are disposed at the same location or different locations. For example, an organization may install one or more medical devices 102, 104, and/or 106 at various facilities, in various geographic locations, and/or the like. In embodiments, the medical devices 102, 104, and/or 106 may be managed by a single entity or different entities. As shown, different medical devices 102, 104, and 106 may be configured to communicate with other devices using different types of networks, combinations of networks, and/or the like. For example, medical devices 102 and 104 may be configured to communicate via a wireless local access network (WLAN) 112, while medical device 106 may be configured to communicate via a cellular network 114. In embodiments, the medical devices 102, 104, and/or 106 may include technology that enables communication through different types of networks, thereby enabling a medical device 102, 104, and/or 106 to transition from one type of network to another.

According to embodiments, the medical devices 102, 104, and/or 106 are configured to provide information, such as, device-readiness information, device performance information, clinical event information, and/or the like, to the management server 108. Device-readiness information or data may include any information associated with the condition of one or more components of the medical device that may have bearing on the ability of the medical device to perform a function for which it was designed. For example, device-readiness information may include information associated with a condition, status, and/or remaining life of a battery or batteries, an electrode, a sensor, a communication component, and/or the like. Device performance information or data may include any information associated with a performance of a component and/or function of the medical device. For example, device performance information may include information about functions a medical device performed during a medical and/or emergent situation such as, for example, a manner in which a defibrillation shock was applied during a cardiac arrest situation, an energy level of an applied shock during the situation, a number of times a shock was applied during the situation, and/or the like. Clinical event information or data may include any information, recorded during a clinical event, associated with a patient. For example, clinical event information may include physiological parameters, patient demographic information, patient ECG data, device prompting records, device actions and operations, CPR performance data, faults, errors, and/or voice recording, and/or the like.

The medical devices 102, 104, and/or 106 are communicably coupled to the management server 108, and, in some embodiments, are configured to communicate directly with the management server 108, while, in other embodiments, the medical devices 102, 104, and/or 106 are configured to communicate with a collection server 116, which is configured to communicate with the management server 108. In embodiments, to improve efficiencies all of the medical devices 102, 104, and/or 106 may be configured to provide information to the management server 108 by transmitting the information to a single uniform resource locator (URL). Although the management server 108 and the collection server 116 are each referred to herein in the singular, the management server 108 and the collection server 116 may be implemented in multiple server instances (for example, as a server cluster), distributed across multiple computing devices, instantiated within multiple virtual machines, and/or the like.

As shown in FIG. 1, user devices 118 and 120 may be communicably coupled to the management server 108 and may be configured to access services provided by the management server 108. For example the management server 108 may facilitate providing information received from the medical devices 102, 104, and/or 108 to the user devices 118 and/or 120. Additionally, users may utilize the management server 108, via the user devices 118 and/or 120, to configure the medical devices 102, 104, and/or 108, to provide software updates to them, and/or the like.

As used herein, the phrase "communicably coupled" is used in its broadest sense to refer to any coupling whereby information may be passed. Thus, for example, communicably coupled includes electrically coupled by, for example, a wire; optically coupled by, for example, an optical cable; and/or wirelessly coupled by, for example, a radio frequency or other transmission media. "Communicably coupled" also includes, for example, indirect coupling, such as through a network or a series of devices and/or communication protocols, or direct coupling.

The illustrative operating environment 100 shown in FIG. 1 is not intended to suggest any limitation as to the scope of use or functionality of embodiments of the present disclosure. Neither should the illustrative operating environment 100 be interpreted as having any dependency or requirement related to any single component or combination of components illustrated therein. Additionally, any one or more of the components depicted in FIG. 1 or described herein may be, in embodiments, integrated with various ones of the other components depicted therein (and/or components not illustrated), all of which are considered to be within the ambit of the present invention. For example, the collection server 116 may be integrated with the management server 108, and the network 110 may be included, or be included within, the WLAN 112, and/or the cellular network 114.

According to embodiments, various components of the operating environment 100, illustrated in FIG. 1, can be implemented on one or more computing devices. For example, one or more of the medical devices 102, 104, 106; the management server 108, the collection server 116, and the user devices 118 and 120 may include, be communicatively coupled to, and/or be included within, one or more computing devices. A computing device may include any type of computing device suitable for implementing embodiments of the invention. Examples of computing devices include specialized computing devices or general-purpose computing devices such "workstations," "servers," "laptops," "desktops," "tablet computers," "hand-held devices," components of medical devices, and/or the like, all of which are contemplated within the scope of FIG. 1 and reference to various components of the operating environment 100.

Figure 2:
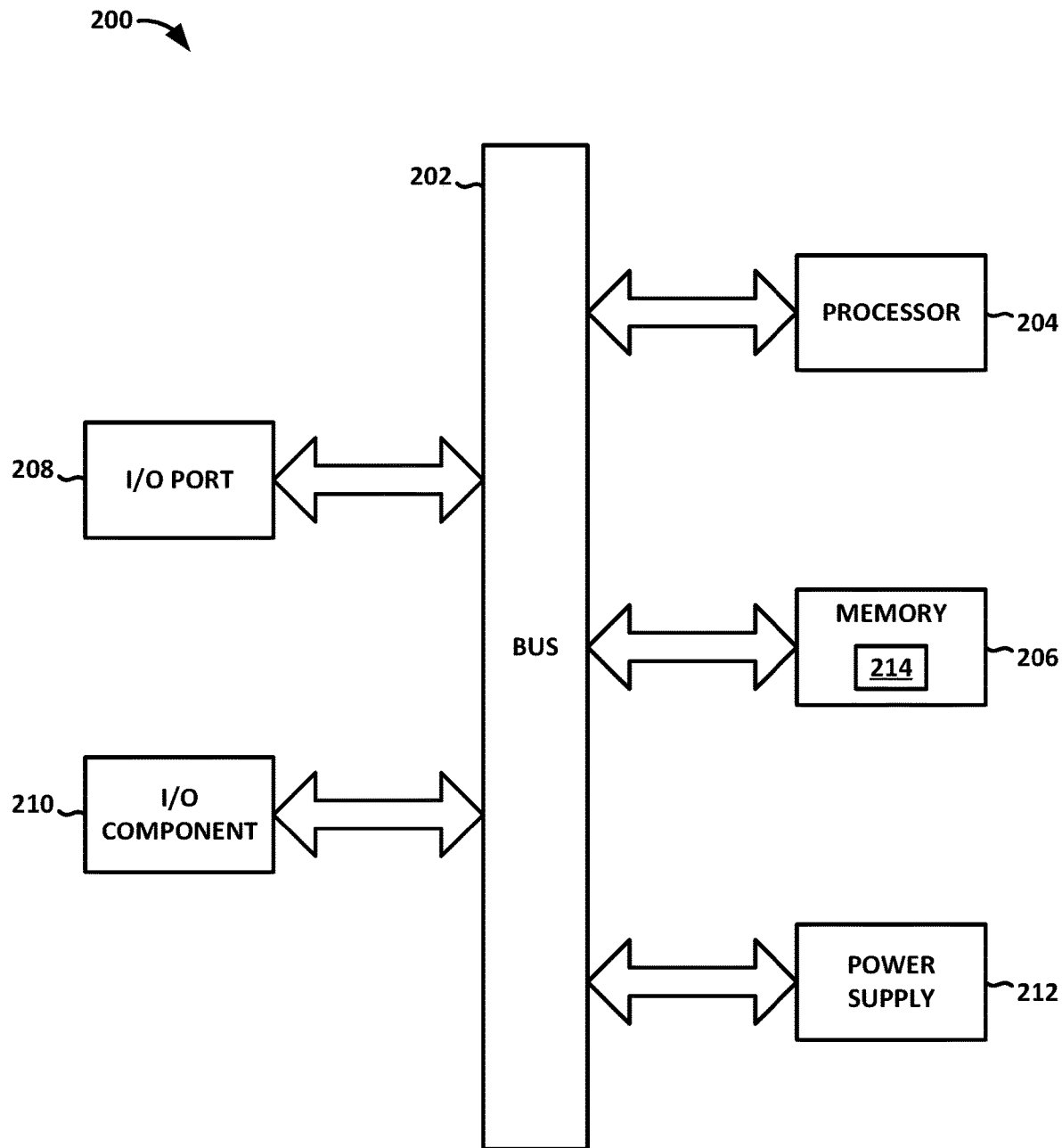
FIG. 2 depicts an illustrative computing device in accordance with embodiments of the present disclosure.

As shown in FIG. 2, a computing device 200 includes a bus 202 that, directly and/or indirectly, couples one or more of the following devices: a processor 204, a memory 206, an input/output (I/O) port 208, an I/O component 210, and a power supply 212. Any number of additional components, different components, and/or combinations of components may also be included in the computing device 200. The bus 202 may represent one or more busses (such as, for example, an address bus, data bus, and/or combination thereof). Similarly, in embodiments, a computing device 200 may include a number of processors 204, a number of memory components 206, a number of I/O ports 208, a number of I/O components 210, and/or a number of power supplies 212. Additionally, any number of these components, and/or combinations thereof, may be distributed and/or duplicated across a number of computing devices 200.

Although the various components of FIG. 2 are shown as distinct components for the sake of clarity, in reality, delineating various components of a computing device 200 may not be as clear. For example, I/O components 210 may include devices contained within the computing device 200 and/or devices that are separate from the computing device 200. As another example, processors 204 may have memory. As such, the diagram of FIG. 2 is merely illustrative of an example of a computing device 200 that may be used in connection with one or more embodiments, but any number of other configurations for a computing device 200 that can execute computer-executable instructions to accomplish various aspects of embodiments described herein are also considered to be within the ambit of the invention.

According to various embodiments, the processor 204 (or processors) reads data from various entities such as the memory 206, I/O components 210, and/or the like. For example, in embodiments, the processor 204 may execute computer-executable instructions 214 that are stored in the memory 206. Additionally, in embodiments, the processor 204 may receive computer-executable instructions, signals, and/or other types of information from one or more I/O components 210. As the processor 204 reads and manipulates information, it may also cause information to be stored in the memory 206.

In embodiments, the memory 206 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; or any other medium that can be used to encode information and can be accessed by a computing device such as, for example, quantum state memory, and/or the like.

Figure 3:
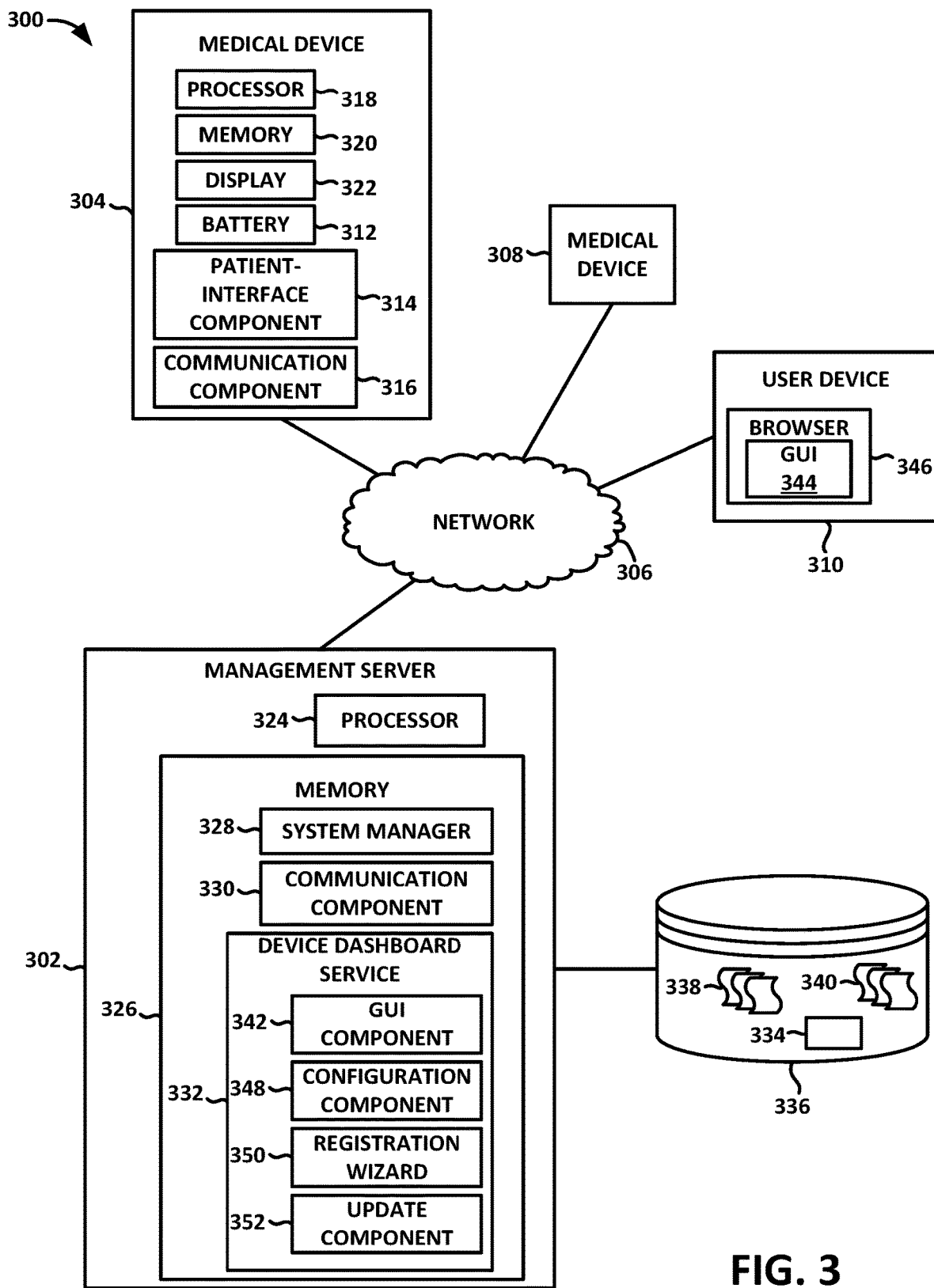
FIG. 3 depicts another illustrative operating environment in accordance with embodiments of the present disclosure.

In embodiments, the memory 206 stores computer-executable instructions for causing the processor 204 to implement aspects of embodiments of system components discussed herein and/or to perform aspects of embodiments of methods and/or procedures discussed herein. Computer-executable instructions may include, for example, computer code, machine-useable instructions, and the like such as, for example, program components capable of being executed by one or more processors associated with a computing device. Examples of such program components are depicted in FIG. 3, and may include the system manager 328, the communication component 330, the device dashboard 332 (and components thereof), the database 336, and/or the like. Some or all of the functionality contemplated herein may also, or alternatively, be implemented in hardware and/or firmware.

In embodiments described herein, upon being executed by one or more processors, computer-executable instructions may cause the one or more processors to initiate one or more components, e.g. a communication component. The components may be, or include, program components, electrical circuits, logic modules, mechanical assemblies, and/or any number of different types of combinations of hardware, firmware, and software. As the term is used herein, "initiate" may include instantiate, create, activate, utilize, and/or the like. That is, for example, the components initiated by a processor may be software components created, instantiated, or otherwise invoked by the processor. As another example, the components may include hardware (for example, electronic circuits) activated by the processor. As such, a "component" which may also be referred to as a "module" may be initiated and/or implemented in, or as a combination of two or more of, hardware, software, and firmware, and may be initiated and/or instantiated and/or located in one device or place, or alternatively distributed across multiple devices and/or places and/or in the network 110 or the cloud.

In embodiments, the I/O port 208 may allow the computing device 200 to be logically coupled to other devices including external devices and/or I/O components 210, some of which may be built in. Examples of I/O components 210 include a microphone, joystick, game pad, satellite dish, scanner, printer, wireless device, keyboard, pen, voice-input device, touch-input device, touch-screen device, interactive display device, a mouse, and the like. In embodiments the I/O component 210 may include, for example, a presentation component (for example, a display, a printing device, a touch-screen I/O display, etc.), a communication component (for example, a transceiver, an antenna, etc.), and/or the like.

The illustrative computing device 200 shown in FIG. 2 is not intended to suggest any limitation as to the scope of use or functionality of embodiments of the present disclosure. Neither should the illustrative computing device 200 be interpreted as having any dependency or requirement related to any single component or combination of components illustrated therein. Additionally, any one or more of the components depicted in FIG. 2 may be, in embodiments, integrated with various ones of the other components depicted therein (and/or components not illustrated), all of which are considered to be within the ambit of the present invention.

FIG. 3 depicts an illustrative operating environment 300 in accordance with embodiments of the invention. The illustrative operating environment 300 includes a management server 302 that is configured to communicate with a medical device 304 via a network 306. Any number of additional medical devices 308 may be configured to communicate with the management server 302, as well. The communication between the management server 302 and the medical device 304 and/or 308 may be unidirectional or bidirectional. According to embodiments, a user may utilize a user device 310 to communicate with the management server 302. The management server 302 may be (or be similar to), for example, the management server 108 depicted in FIG. 1; the medical device 304 and/or 308 may be (or be similar to), for example, the medical devices 102, 104 and/or 106 depicted in FIG. 1; the network 306 may be (or be similar to) any one or more of the networks 110, 112, and 114 depicted in FIG. 1; and the user device 310 may be (or be similar to) the user devices 118 and/or 120 depicted in FIG. 1.

The medical device 304 may be powered by one or more batteries 312 and may include a patient-interface component 314 configured to provide treatment to, and/or obtain physiological parameter measurements from, a patient; and a communication component 316 configured to facilitate transmitting information through the network 306 to the management server 302. In embodiments, the patient-interface component 314 may be, or include, one or more defibrillation electrodes (pads), one or more infusion needles, and/or the like. The medical device 304 also may include a processor 318 and a memory 320.

The medical device 304 may receive signals from one or more patient-interface components 314 (for example, sensors or electrodes) coupled to a patient and use the processor 318 to analyze the signals to monitor, detect, and/or derive or calculate various physiological parameters. For example, the processor 318 may monitor, detect, and/or derive or calculate heart rate, blood pressure, temperature, respiration rate, blood oxygen level, end-tidal carbon dioxide level, pulmonary function, blood glucose level, weight, and/or the like. Any one or more of these physiological parameters, other measured parameters, other derived parameters, and/or the like may be stored in the memory 320. In some embodiments, the medical device 304 includes a display 322 for presenting data associated with one or more of the above physiological parameters, other clinical event information, configuration options, and/or the like. Clinical event information (for example, physiological parameters, device usage metrics, and/or the like, recorded during use of the medical device 304 during a clinical event), self-test information, configuration information, and/or the like may be stored in the memory 320.

The communication component 316 may include I/O ports (for example, logical ports, virtual ports, physical ports, etc.), one or more antenna, one or more transceivers, one or more receivers, and/or the like. In embodiments, for example, the communication component 316 may include I/O ports such as, for example, an RS-232 port for use with a modem based dialup connection, a copper or fiber 10/100/ 1000 Ethernet port, a Bluetooth® or WiFi interface, an infrared port, a universal serial bus (USB) port, and/or the like. In embodiments, the communication component 316 may be configured to facilitate near-field communications, cellular communications, and/or the like.

In embodiments, the medical device 304 may be configured to transmit information to the management server 302, receive communications from the management server 302, and/or facilitate management of patient data, device status and history, device error logs, and/or the like. The medical device 304 may be configured to receive software updates and configuration information via the communication component 316. In embodiments, the medical device 304 may be configured to transmit self-test information, clinical event information, alarm information, to the management server 302 automatically (for example, according to a programmed schedule, in response to an event, and/or the like) and/or manually (for example, in response to a user input).

As shown in FIG. 3, the management server 302 may be implemented on a computing device that includes a processor 324 and a memory 326. In embodiments, the management server 302 may refer to hardware, software, firmware, or a combination of these, and may be, or include, a computing device, a number of computing devices, a virtual machine, a number of virtual machines, a service, and/or the like. For example, the management server 302 may be a stand-alone server device or server bank. In embodiments, the management server 302 may be software configured to be executed by a computing device such as, for example, the user device 310. Various program components such as, for example, a system manager 328, a communication component 330, and/or device dashboard service 332 may be stored in the memory 326. In embodiments, the processor 324 executes the system manager 328, the communication component 330, and/or the device dashboard service 332.

The system manager 328 may facilitate management of various aspects of the medical devices 304 and/or 306, the device dashboard service 330, and/or the like. For example, the system manager 328 may be configured to coordinate communications between the management server 302 and the medical devices 304 and/or 306; facilitate login and authentication procedures; create, delete, manipulate, and manage user accounts and account information 334 stored in a database 336; interact with, query, and/or index the database 336; facilitate integration with other systems (for example, electronic medical record (EMR) systems, administration systems, and/or insurance/billing systems); facilitate operations and procedures for maintaining compliance with relevant laws and regulations; facilitate configuration and/or customization of various aspects of embodiments of the management server 302; and/or the like. The database 336 may be, or include, one or more tables, one or more relational databases, one or more multi-dimensional data cubes, one or more non-relational databases, and/or the like. Further, though illustrated as a single component, the database 336 may, in fact, be a plurality of databases 336 such as, for instance, a database cluster, which may be implemented on a single computing device or distributed among a number of computing devices, memory components, and/or the like.

The communication component 330 may include similar aspects as the communication component 316 of the medical device 304, and may be configured to communicate with the communication component 316 of the medical device 304. This communication between communication component 330 and communication component 316 may be direct device-to-device communication, and/or indirect communication via network 306 and/or via one or more other devices 308, 310, 336. In embodiments, the operating environment 300 may include a collection server (such as, for example, the collection server 112 depicted in FIG. 1), in which case the communication component 330 may be configured to communicate with a communication component of the collection server, which may be configured to communicate with the communication component 316 of the medical device 304. In embodiments, the communication component 330 may also be configured to facilitate communications between the management server 302 and the medical device 308, the user device 310, other devices, other systems, and/or the like.

In embodiments, the communication component 330 may be configured to receive device-readiness information 338, device performance information, and/or clinical event information 340 from the medical devices 304 and/or 308, e.g. wirelessly. The received information 338 and/or 340 may be stored in the database 336, as shown. According to embodiments, the communication component may also be configured to receive information (for example, device-readiness information, device performance information, and/or clinical event information) from a USB flash drive, a CD-ROM disc, and/or any number of other storage and/or transmission media.

Figure 5:
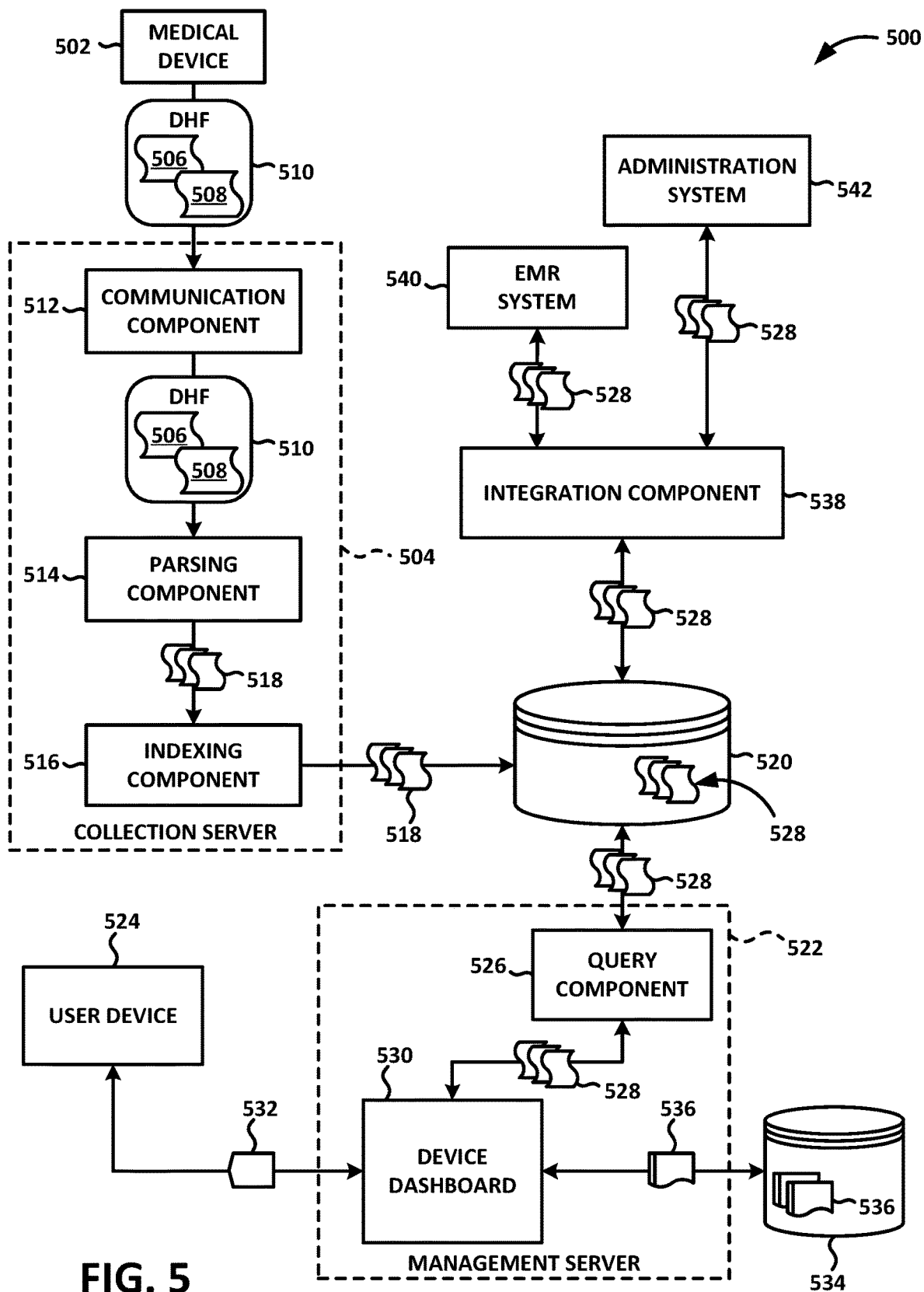
FIG. 5 depicts an illustrative operation of an operating environment in accordance with embodiments of the present disclosure.

Although communication components 316 and 330 (and 512) are shown as boxes associated with devices in FIGS. 3 and 5, as described above such "components" or "modules" may be initiated and/or implemented in, or as a combination of two or more of, hardware, software, and firmware, and may be initiated and/or instantiated and/or located in one device or place, or alternatively distributed across multiple devices and/or places. For example, any one of communication components 316, 330, and/or 512, may be hardware, software, firmware, or some combination thereof, and may be initiated in or on the same device that is collecting information or data being communication, distributed across multiple devices, and/or on a device different from the device that is collecting the information or data being communicated.

According to embodiments, the device dashboard service 332 may be an application configured to assist users with the management of their medical devices. The device dashboard service 332 may serve as a central location for a user to manage their medical devices. Access to the device dashboard service 332 may be web based with the option for customers to add the application to their computer system/network. The device dashboard service 332 may be configured to be compatible with any number of different medical devices and may be configured to allow the user to input additional information about their medical devices, competitor devices, and/or the like. In this manner, the device dashboard service 332 may, in embodiments, facilitate organizing and simplifying medical device management remotely monitoring medical devices; remotely managing AED software; remotely configuring medical devices; viewing clinical event information; viewing device-readiness (self-test) information; and/or the like.

According to embodiments, the device dashboard service 332 may be configured to facilitate management of the medical devices 304 and 306, information received from the medical devices 304 and 306, and/or the like. As shown in FIG. 3, the device dashboard service 332 includes a graphical user interface (GUI) component 342 that is configured to facilitate display of a GUI 344 on the user device 310 (which may include a display (not shown)). Although the GUI 344 is illustrated as being rendered using a browser 346 running on the user device 310, in embodiments, the GUI 344 may be provided using a client application, a browser plug-in, an application plug-in, application programming interface (API), and/or the like. The GUI 344 may facilitate presenting any number of different types of information to a user, including, for example, device-readiness information; device performance information, clinical event information; configuration information; information associated with software status and/or updates; location information corresponding to medical devices; user information; account information; and the like.

In embodiments, for example, the medical device 304 may be an AED and the GUI 344 may be configured to display the following device information, generated from a self-test report: result of the most recent self-test; device serial number; electrode status/expiration; battery status/expiration; device software revisions; device user ID (if programmed); and/or device self-test interval. A failed self-test may result in the aggregation and display of information such as, for example, integration device "failed" self-test; reason for failed self-test, if applicable; and/or the like.

According to embodiments, the device dashboard service 332 may be configured to cause the GUI component 342 to provide reports that may be displayed using the GUI 344, printed, forwarded, and/or the like. For example, on a periodic basis, the device dashboard service 332 may notify a user of a passed self-test via email, the GUI 344, and/or the like. In another example, a daily, weekly, and/or monthly report may be provided. Additionally, in embodiments, reports, alerts, and/or other types of data may be provided to a user via email, short message service (SMS) messaging, and/or the like.

According to embodiments, the management server 108, 302 may be configured to receive, manage, and present device-readiness information or data. The device dashboard service 332 may be configured to provide the user with up-to-date information on the readiness of the medical device 304. This information may include: device-readiness (for example, an indication as to whether the medical device 304 passed the latest self-test), electrode expiration/readiness, and battery information (for example, whether the battery contains enough power for a minimum of 1 rescue). According to embodiments, the management server 108, 302 may be configured to receive, manage, and present device performance information or data.

According to embodiments, the management server 108, 302 also may be configured to receive, manage, and present clinical event information or data. The device dashboard service 332 may be configured to provide the user with complete event information once downloaded from the medical device 304. This data may be downloaded in a Health Insurance Portability and Accountability Act (HIPAA) compliant manner. When downloaded the user may be able to view device actions and prompts, along with basic device information in a main screen. From this main screen the user may be able to navigate to additional tabs such as, for example, ECG and CPR analysis. Upon download of clinical event information, the device dashboard service 332 may be configured to provide display of prompts and/or basic information in languages, in which the medical device recorded the data. According to embodiments, the clinical event information may include event logs and device prompt logs, ECG and waveforms; CPR analysis; CPR quality prompts and screens.

The device dashboard service 332 further includes a configuration component 348 configured to provide configuration information to the medical device 304 and/or 308. In embodiments, a medical device 304 may be configurable based on a number of different options that may be selected by a user. The user may be able to configure the medical device 304 by providing user input directly to the medical device 304, by providing configuration information to the medical device 304 via the configuration component 348, and/or the like. In embodiments, for example, the configuration component 348 may receive user input via the GUI 344 to configure various configuration options. The configuration information (including the configured options) may be provided to the medical device 304 using the configuration component 348. In embodiments, for example, configuration information may be provided, in a configuration file, to the medical device 304, which may be configured to read and parse the configuration file, extract the configuration information, and configure itself based on the configuration information. The device dashboard service 332 may enable a user to provide the same configuration information to all medical devices (of a similar type) that the user is managing, unique configuration information to each medical device, and/or various combinations of the above. According to embodiments, the configuration component 348 may provide configuration information that is transmitted over the network 306 to the medical device 304, downloaded to a storage medium (for example, a USB flash drive), and/or the like.

Any number of different options, features, settings, and/or the like, may be configured using configuration information. The types of configuration options features, and/or settings that are available to be configured by a user may be based on a role assigned to the user, regulatory compliance limitations, safety considerations, and/or the like. In embodiments, for example, the medical device 304 may be an AED, and the configuration options and parameters depicted in Table 1, below, may be available to a user of a first type (for example, a non-administrator), while the configuration options and parameters depicted in Table 2, below, may be available to a user of a second type.

TABLE 1

User Configurable Options

| # | Configurable Option | Possible Values |
|---|---|---|
| T1 | Lay Rescuer Prompts<br>When this option is checked (On), the unit issues the following voice and text prompts after completion of the power-on self-test and entry into clinical mode:<br>STAY CALM<br>CHECK RESPONSIVENESS<br>CALL FOR HELP<br>Lay Rescuer prompts will only be issued prior to pad placement. If pads are pre-attached the lay rescuer prompts will NOT be issued. | On<br>Off |
| T2 | CPR Countdown Timer<br>The AED Plus 2 will display a visual indication for remaining time in CPR/compression cycle | On<br>Off |
| T3 | Language<br>User configurable for up to three (3) languages<br>Languages must be individually loaded<br>Dependent on ordered languages | Language 1<br>Language 2<br>Language 3 |
| T4 | Transfer<br>User can:<br>Transfer via a USB flash drive or through a WiFi connection. | Transfer via WiFi or USB:<br>Clinical event file<br>Device History<br>Configuration |
| T5 | Set Time & Date<br>Allows user to manually set the time on the AED Plus 2 (Ability to set DST) | 00:00<br>Month/Day/Year<br>DST |
| T6 | CPR Depth Measure of Units | Inches (IN)<br>Centimeters (CM) |
| T7 | Lay Breathing Prompt<br>Allows you to configure the "Lay Breathing" prompt of "Open Airway, Check Breathing", based on the guidelines you want to follow.<br>When disabled (Off), these prompts are not issued. | On<br>Off |

TABLE 2

Administrator Configurable Options

| # | Configurable Option | Possible Values |
|---|---|---|
| 1 | Self Test Interval<br>Sets the period of time between automated self-tests in standby state. | 1 day<br>7 days |
| 2 | Auto Self-Test Report<br>Following the pre-configured self-test the AED Plus 2 will attempt to link with ZOLL Online/En-Pro through a WiFi connection. | On<br>Off |

TABLE 2-continued

Administrator Configurable Options

| # | Configurable Option | Possible Values |
|---|---|---|
| 3 | CPR Recording<br>When this option is checked (On) and pads with a CPR sensor are attached, the unit performs CPR monitoring, prompts the rescuer, and records chest compressions in the event data file. (Real CPR Help ®). When this option is Off, the unit does the same-BUT does NOT record chest compressions. | On<br>Off |
| 4 | Breathe During CPR Prompt<br>The AED Plus 2 will prompt "Give Two Breaths" every 30 recognized compressions | On<br>Off |
| 5 | Adult First Shock Energy<br>Sets the energy level in joules for the first shock for an adult patient. | 120 J<br>150 J<br>200 J |
| 6 | Adult Second Shock Energy<br>Note: This value cannot be less than the value selected for the first adult shock. | 120 J<br>150 J<br>200 J |
| 7 | Adult Third Shock Energy<br>Note: This value cannot be less than the value selected for the second adult shock. | 120 J<br>150 J<br>200 J |
| 8 | Pediatric First Shock Energy<br>Sets the energy level in joules for the first shock for a pediatric patient. | 50 J<br>70 J<br>85 J |
| 9 | Pediatric Second Shock Energy<br>Note: This value cannot be less than the value selected for the first pediatric shock. | 50 J<br>70 J<br>85 J |
| 10 | Pediatric Third Shock Energy<br>Note: This value cannot be less than the value selected for the second pediatric shock. | 50 J<br>70 J<br>85 J |
| 11 | No Shock CPR Period<br>Sets the duration of the CPR period following a No Shock Advised result for the analysis. | 30 seconds<br>60 seconds<br>90 seconds<br>120 seconds<br>150 seconds<br>180 seconds |
| 12 | Post Shock CPR Period<br>Sets the duration of the CPR period following the delivery of a shock. | 30 seconds<br>60 seconds<br>90 seconds<br>120 seconds<br>150 seconds<br>180 seconds |
| 13 | Start with CPR Period<br>Configures the AED Plus 2 to start with CPR once electrodes are attached to the patient. | Off<br>30 seconds<br>60 seconds<br>90 seconds<br>120 seconds<br>150 seconds<br>180 seconds |
| 14 | Continue CPR Prompt<br>"Continue CPR" will be repeated once every N* seconds (see parameter 15) if CPR compressions stop during the CPR interval. When this option is set to Off, the "Continue CPR" prompt will not be issued during the CPR period. | On<br>Off |
| 15 | CPR Prompt Interval<br>This option determines the interval for the following prompts:<br>Real CPR Help ®<br>START CPR<br>CONTINUE CPR | 10 seconds<br>15 seconds |
| 16 | Set Supervisor Passcode<br>Allows user to change the passcode used to enter Supervisor mode | 1 2 3 4 5 6<br>_ _ _ _ _ _ |
| 17 | Device Identifier (defaults to SN of device) | Allows input of 11 digit alpha-numeric device ID. |
| 18 | User Transfer via USB or WiFi<br>User can transfer the:<br>Configuration file (device and WiFi settings)<br>Device History Report<br>Clinical Event Data | Transfer via WiFi or USB:<br>Configuration file<br>Device History Report<br>Clinical Event Data |
| 19 | Install (USB)<br>User can install:<br>Configuration file<br>Software upgrade<br>Language file | Install via USB flash drive:<br>Configuration file<br>Software upgrade<br>Language file |

TABLE 2-continued

Administrator Configurable Options

| # | Configurable Option | Possible Values |
|---|---|---|
| 20 | Number of Clinical Cases<br>User can configure number of clinical cases the AED Plus 2 will store for both audio and non-audio devices | 1<br>2 |
| 21 | Voice Recording<br>Note: Option will only be available when a customer orders an "AED Plus 2 Pro" device. Default will be "OFF" on enabled devices. | On<br>Off |
| 22 | Device Display<br>Allows user to select information displayed on the LCD during clinical use. | Lay Rescuer<br>ECG and CPR Dashboard<br>ECG<br>CPR Dashboard |
| | Lay Rescuer | Default AED Plus 2 display with animations. |
| | ECG and CPR Dashboard | The AED Plus 2 will display the patient's ECG rhythm and all text prompts. During the CPR cycle the CPR Dashboard will also be active. |
| | ECG | The AED Plus 2 will display the patient's ECG rhythm and text prompts. |
| | CPR Dashboard | Text prompts will be displayed. During the CPR Cycle the CPR Dashboard will also be active. |

As shown in FIG. 3, the device dashboard service 332 may also include an update component 350 configured to provide software updates to the medical device 304. According to embodiments, the update component 352 may provide software updates that are transmitted over the network 306 to the medical device 304, downloaded to a storage medium (for example, a USB flash drive), and/or the like. Additionally, the update component 352 may be configured to enable scheduled software updates, periodic software updates, and/ or the like.

In embodiments, the device dashboard service 332 may include a customer registration wizard 350 configured to assist a user in registering to use one or more services provided by the management server 302. The customer registration wizard 350 may be configured to walk a user through a registration process, gather various types information from the user, and send the information to various appropriate services, databases, entities, and/or the like. For example, the registration wizard 350 may solicit, and/or facilitate the creation of, login credentials corresponding to a particular user device, user, organization, medical device, group of medical devices, user account, and/or the like. These login credentials may be provided to a first service and/or entity. The registration wizard 350 may be configured to solicit, and/or facilitate the creation of, account set-up information, which may be provided to a second service and/or entity. Additionally, for example, the registration wizard 350 may be configured to solicit device warranty registration information, which may be provided to a third service and/or entity. Any number of different types of information may be requested from a user and/or generated during a registration procedure and the registration wizard 350 may facilitate providing any number of different types of information to any number of different service and/or entities.

During a registration process, a user may configure any number of various aspects, features, options, and/or the like, associated with the device dashboard service 332. In embodiments, for example, a user may be able to specify a notification frequency, which may be a frequency with which the medical device 304 is configured to communicate information to the management server 302. The device dashboard service 332 may, in embodiments, facilitate tiered device management, grouping medical devices based on geography, selection of the language to be used, providing portals for distribution partners, and/or the like.

According to embodiments, the device dashboard service 332 may facilitate user role-based permissions. That is, in embodiments, each user associated with a particular account, group of medical devices, and/or the like, may be assigned a particular role that defines the level of access the user has to various types of information, functionality, and/or the like. The device dashboard service 332 may also identify responsibilities of each user and implement mechanisms for tracking their relative performance, regulatory compliance, internal policy compliance, and/or the like. In embodiments, the device dashboard service 332 may be configured to manage a number of different user types associated with each type of medical device.

As an example, the device dashboard service 332 may be configured to recognize various types of users associated with AEDs. That is, for example, the device dashboard service 332 may recognize five main user roles associated with AED devices themselves: AED Maintainer; AED Program Manager; AED Rescuer; Medical Director; and Medical Doctor. Although these user roles associated with AEDs are described herein for the purposes of clarity and illuminating possible implementation concepts, embodiments of the invention facilitate supporting any number of different user roles associated with any number of different types of medical devices.

According to embodiments, an AED Maintainer may be tasked with maintaining a fleet of AEDs (for example, 1-100+ AEDs). The AED Maintainer may be responsible for ensuring that all AEDs are in working order, are up to date, have current electrodes and batteries, and/or the like. An AED Program Manager may, for example, be tasked with managing a number of locations at which an AED Maintainer is present. The AED Program Manager may have responsibility over an entire AED Program (corporate/school district/military base, and the like), ensuring that all locations are meeting internal and external requirements. In embodiments, the AED Program Manager may be provided the ability to view information associated with all AEDs for which he or she is responsible through a hierarchical system. The AED Rescuer may operate the AED during a clinical patient event.

In embodiments, the Medical Director may provide medical direction over a number of AEDs. The Medical Director's responsibilities may include, for example, ensuring that all of the AEDs under the Medical Director's care are properly maintained; ensuring that all AED sites have up-to date CPR/AED Certified responders; providing post-event support and/or clinical event data review. Thus, for example, the Medical Director may be provided the ability to quickly view locations that they are in charge of managing to confirm compliance with various aspects of AED management, such as, for example, to confirm device-readiness and the preparedness of a location to respond to a medically emergent situation. Additionally, in embodiments, the Medical Doctor may be provided with the ability to view clinical event information closely following the clinical use of an AED.

Similarly, the device dashboard service 332 may be configured to recognize a number of dashboard user roles. For example, in embodiments, dashboard users may have responsibility over the management and maintenance of an AED or multiple AEDs. Additionally these users may have responsibility for the download and/or review of clinical event information. In embodiments, these users may be assigned one or more of four user roles: administrator, site-user, medical director/doctor, and EMS Agencies.

For example, an administrator may be responsible for the management of multiple AEDs spread over multiple locations. The locations may vary (for example, by state, country, town, or the like) with each site having a specific responsible user. The administrator may be responsible for the management of all sites, groups of sites, and/or the like. Illustrative activities related to an administrator's responsibility may include ensuring compliance with "Good Samaritan" laws, ensuring AED program compliance, ensuring device-readiness, providing CPR/AED training, and facilitating device configuration. In embodiments, the administrator's primary task may not involve AED device management, as the management of an AED program may be an assigned task.

In embodiments, a site-user may be responsible for all AEDs associated with an individual location. The site user may report to an administrator as their site could be one of multiple locations associated with one customer. Illustrative activities related to a site-user's responsibility may include ensuring device-readiness, device performance, training of an emergency response team, and/or the like. A medical director/doctor may have responsibility over multiple AEDs at multiple locations, and may be a prescribing physician. The medical director/doctor may be responsible over AEDs deployed in multiple locations. They may be responsible for ensuring that all sites maintain their AEDs properly and are compliant with training certifications. Additionally, the medical director/doctor also may provide post-event support and may review clinical event information. Illustrative activities related to a medical director/doctor's responsibilities may include tracking individual site compliance, providing post-event support, review of clinical event information, and/or the like. Additionally, in embodiments, EMS Agencies may also be an "administrator" if the EMS service offers a Public Access Defibrillation (PAD) program. Additionally, the device dashboard service 332 may be configured to integrate into EMS response software, for example, to alert dispatchers of the locations of AEDs in close proximity to a cardiac arrest emergency.

According to embodiments, the management server 302, the medical device 304, the user device 310, and/or another system component such as, for example, an administration system (for example, the administration system 542 depicted in FIG. 5), may be configured to process information received from the medical device 304 and, in embodiments, utilize the information and/or processed information to facilitate additional services. For example, in embodiments, any one or more of device-readiness information, device performance information, and clinical event information may be processed to generate statistical reports across geographic areas, customers, devices within a fleet, device types, devices of certain ages, versions, and/or configurations, environmental conditions (for example, elevation, average temperature, temperature ranges, average humidity, humidity ranges, average barometric pressure, barometric pressure ranges, sun-exposure levels and/or durations, atmospheric contaminant types and/or levels, and/or the like), use conditions (for example, frequency of use, nature of use, durations of use, and/or the like), user demographics (for example, user roles, user types, user ages, user experience levels, and/or the like), outcomes (for example, measures of intervention success, prognosis, diagnosis, and/or the like), and/or the like. Reports may be generated periodically, manually, automatically, and/or the like, and may be provided to any number of devices, users, groups of users, regulation authorities, clinicians, and/or the like.

In embodiments, the management server 302, the medical device 304, the user device 310, and/or another system component such as, for example, an administration system (for example, the administration system 542 depicted in FIG. 5), may be configured to facilitate any number of other functionalities, services, and/or features associated with managing a fleet of medical devices. For example, a user may be able to remotely access audio/video equipment associated with the medical device 304, facilitate medical billing and/or other financial transactions, respond to requests for medical information, obscure personally identifiable information, and/or the like.

The illustrative operating environment 300 shown in FIG. 3 is not intended to suggest any limitation as to the scope of use or functionality of embodiments of the present disclosure. Neither should the illustrative operating environment 300 be interpreted as having any dependency or requirement related to any single component or combination of components illustrated therein. Additionally, any one or more of the components depicted in FIG. 3 may be, in embodiments, integrated with various ones of the other components depicted therein (and/or components not illustrated), all of which are considered to be within the ambit of the present invention. For example, a web server (which may include one or more components, features or aspects of the management server 302) may be integrated with the medical device 304, may be accessible by the browser 346, and may be used to manage one or more other medical devices 308. Embodiments of situations in which a medical device 304 includes a web server, in this manner, are disclosed, for example, in U.S. Publication No. 2014/0266794, "PATIENT MONITOR SCREEN AGGREGATION," filed by Brown et al. on Mar. 14, 2014, the entirety of which is hereby incorporated by reference herein, for all purposes.

Figure 4:
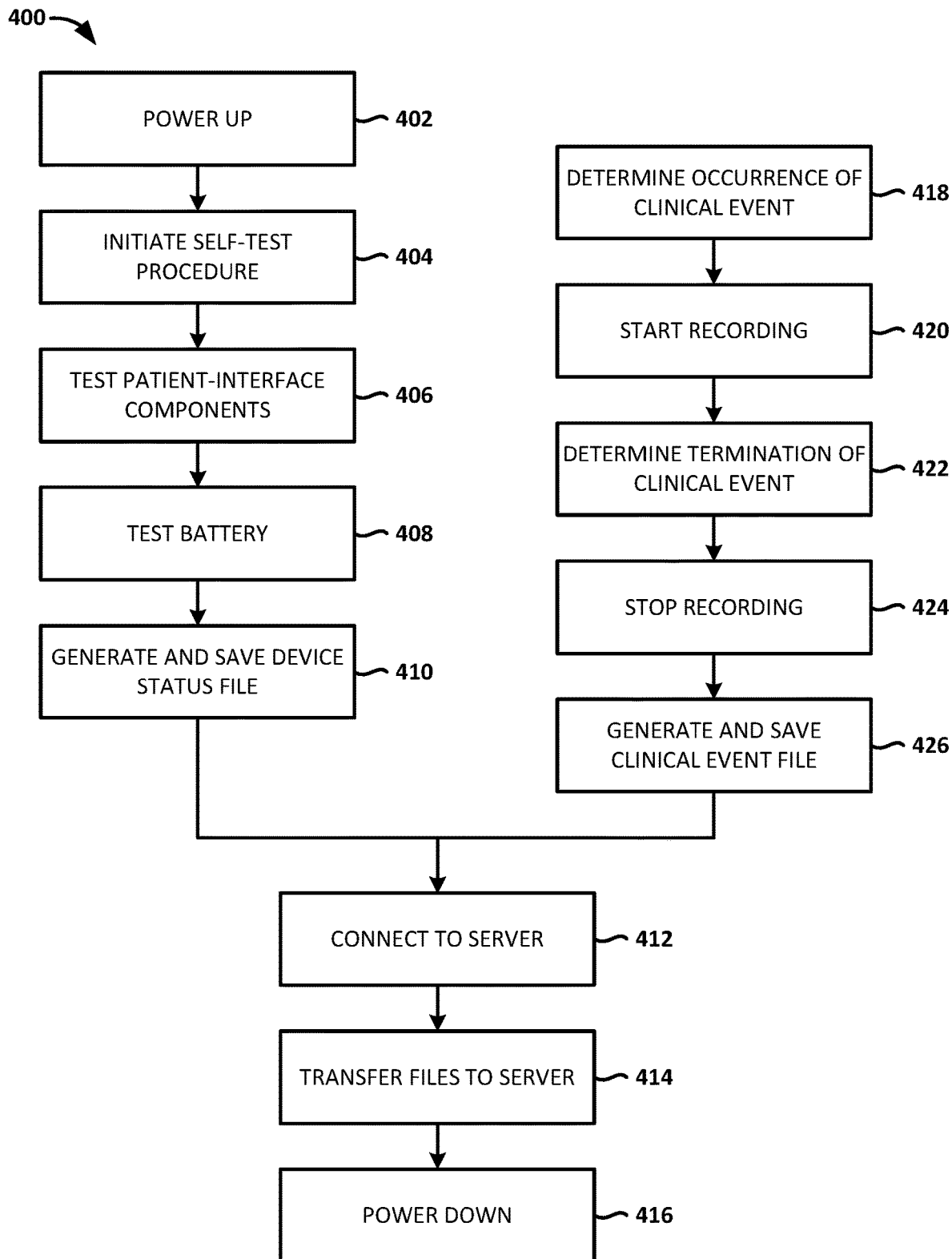
FIG. 4 is a flow diagram depicting an illustrative method of medical device management in accordance with embodiments of the disclosure.

As described above, embodiments of the invention provide a management server configured to facilitate remote management of a number of medical devices and/or information received therefrom. FIG. 4 is a flow diagram depicting an illustrative method 400 of facilitating medical device management in accordance with embodiments of the invention. As shown in FIG. 4, embodiments of the method 400 may be performed by a medical device (for example, the medical devices 102, 104, and/or 106 depicted in FIG. 1; and/or the medical devices 304 and 308 depicted in FIG. 3) and may include powering up (block 402) and initiating a self-test procedure (block 404). In embodiments, the medical device may be configured to initiate the self-test procedure periodically, according to a programmed schedule; upon installation of a battery or batteries; upon being powered up (i.e., turned on); upon receiving a user input; and/or the like.

In embodiments, the self-test procedure may be configured to test any number of different functions, features, and/or the like. As shown in FIG. 4, the illustrative method 400 includes testing patient-interface components (block 406) and testing the battery (or batteries) (block 408). Using the device-readiness information resulting from the self-test procedure, a device status file is generated and saved in a local memory component (block 410). According to embodiments, the self-test procedure may include any number of different protocols and procedures for verifying the ability of patient-interface components, batteries, communication components, and/or the like, to operate safely and effectively when needed.

According to embodiments, patient-interface components may include any type of component configured to facilitate an interaction with a patient such as, for example, therapy-delivery components, sensing components, communication components, and/or the like. For example, in the case of a medical device that is, or includes, an AED, the self-test procedure may include verifying that the defibrillation electrodes are properly connected to the device; verifying that the ECG signal acquisition and processing electronics are functional; verifying that the defibrillator electronics are functional and can charge and discharge at a predetermined level; verifying proper function of the microprocessor electronics and the integrity of the software; verifying that the CPR monitoring and compression depth detection are functional; verifying that voice prompts and/or visual indicators are functional; verifying that adequate battery capacity remains; verifying that the defibrillation electrodes have adequate usable life remaining; and/or the like.

As shown in FIG. 4, the method may further include connecting to a server (block 412), and transferring files to the server (block 414). The server may be, or be similar to, for example, the management server 108 and/or the collection server 116 depicted in FIG. 1, and/or the management server 302 depicted in FIG. 3. Optionally, the medical device may be configured to power down (block 416) after transferring the files to the server. Embodiments of the illustrative method 400 may also include determining the occurrence of a clinical event (block 418) and, in response to determining the occurrence of the clinical event, start recording (block 420). The occurrence or commencement of a clinical event may be determined, in some embodiments, by the placement of the medical device into a therapy or clinical mode. In embodiments, the medical device may be configured to record any number of different types of clinical event information such as, for example, heart rate, blood pressure, temperature, respiration rate, blood oxygen level, end-tidal carbon dioxide level, pulmonary function, blood glucose level, weight, electrocardiograms, and/or the like. The medical device determines when the clinical event has terminated (block 422), stops recording (block 424), and generates and saves a clinical event file (block 426). The clinical event file, containing clinical event information, may be transferred to the server (block 414) along with the device status file, in a separate communication, and/or the like.

FIG. 5 is a schematic block diagram depicting an illustrative operation of an operating environment 500 in accordance with embodiments of the invention. As shown in FIG. 5, the operating environment 500 includes a medical device 502 (for example, an AED) that is communicably coupled to a collection server 504. The medical device 502 may be (or be similar to), for example, the medical devices 102, 104, and/or 106 depicted in FIG. 1, and/or the medical devices 304 and/or 308 depicted in FIG. 3; and the collection server may be (or be similar to), for example, the collection server 116 depicted in FIG. 1. In embodiments, the medical device 502 may be configured to perform periodic self-tests to evaluate the condition of one or more batteries, one or more patient interface components (for example, electrodes), and/or the like. The results of the self-tests may be stored, as device-readiness information, in a local memory on the medical device 502. The device-readiness information may include, for example, the date and time of the self-test, the type of self-test performed, and/or the results of the self-test.

The medical device 502 is configured to communicate the device-readiness information 506, as well as clinical event information 508, to the collection server 504, which may be, for example, a software-as-a-service (SaaS) implementation hosted on the cloud, independent of the geographical site of the medical device 502. The medical device 502 may also communicate, to the collection server 504, performance data, maintenance logs, a device identifier (ID), a device serial number, and/or the like. In embodiments, the medical device 502 may include a global positioning system (GPS), or other location-identifying technology, and may communicate location information to the collection server 504. In other embodiments, the medical device 502 does not include a GPS or other location-identifying technology, in which case no location information is communicated to the collection server 504. In embodiments, a device ID may be configured to include, within its text, information about the location of the medical device 502. In embodiments, the various types of information may be sent from the medical device 502 to the collection server as a Device History File (DHF) 510. The DHF 510 may be, for example, a file configured using a proprietary file format and communicated over standard HTTP/SSL. According to embodiments, the DHF 510 may be configured using any number of different formats and may be communicated using any number of different communication protocols.

According to embodiments, the medical device 502 may initialize communication with the collection server 504 in any number of various ways. For example, the medical device 502 may initiate communication manually (for example, in response to user input to the medical device 502), automatically (for example, according to a predetermined schedule, in response to an event, etc.), and/or the like. In an automatic configuration, the medical device 502 may be configured to attempt to initiate a session with the collection server 504 periodically, upon receiving the DHF 510, and/or according to any other configured schedule. In embodiments, if the medical device 502 fails to establish communication with the collection server 504, it may be configured to re-attempt communication initiation a certain number of times before powering down and waiting to attempt to initiate communication again according to the schedule.

As shown, the collection server 504 includes a communication component 512 that is configured to receive the DHF 510 from the medical device 502, a parsing component 514 that is configured to parse the DHF 510, and an indexing component 516 that is configured to save the parsed information 518 in a database 520. The database 520 may include a relational database, a tabular database, a multidimensional data cube, and/or the like. Additionally, the database 520 may represent one or more databases distributed across one or more memory components, computers, and/or the like. According to embodiments, the collection server 504 may be configured to interrogate the medical device 502 and/or may maintain a registry of medical devices with which it communicates; while, in other embodiments, the collection server 504 does not interrogate medical devices and/or does not maintain a registry of medical devices with which it communicates. Information associated with a particular medical device 502 may be indexed according to the device ID and/or serial number corresponding to that medical device 502. In embodiments, the collection server 504 may continue to build the database 520 without purging information contained therein, while in other embodiments, the collection server 504 may continuously or periodically purge information from the database 520 to make room for new information.

In one embodiment, the medical device 502 and/or its communication component 512 is configured to automatically transmit information (e.g. device readiness information, device performance information, device clinical information, and/or other device information) automatically and without request from the server device 504. For example, the medical device 502 may be configured to automatically transmit the information to the server device 504 upon the completion of a device self-test, whether the self-test is scheduled or automatic. In another embodiment, the medical device 502 may be configured to automatically transmit the information according to a schedule, the schedule being stored in a memory on the medical device 502, for example memory 320. In yet another embodiment, the medical device 502 may be configured to automatically transmit the information according to conditions being satisfied; for example, the medical device 502 may be configured to automatically transmit the information when it is powered down (e.g. not in use for a medical emergency) and when a certain period of time has passed since it last sent the information. In yet another embodiment, the medical device 502 is configured to automatically transmit the information after a medical event in which the device 502 has been used, after the device 502 is no longer being used in the event or upon determining that it has been powered down or docked into a docking station. In another embodiment, the medical device 502 is configured to automatically transmit the information when a battery level falls below a certain threshold, and/or when a device readiness fault is noted, and/or when a calculated lifetime for a component within the device 502 has been exceeded, and/or immediately before, during, or immediately after the device 502 is reconfigured and/or having its software updated.

As shown in FIG. 5, the operating environment 500 also includes a management server 522, which may be configured to facilitate user access, via a user device 524, to information obtained from the medical device 502. The management server 522 may be (or be similar to) the management server 108 and/or the collection server 116 depicted in FIG. 1, and/or the management server 302 depicted in FIG. 3. In embodiments, the management server 522 facilitates remote maintenance, monitoring, and/or management of various medical devices 502. In the illustrated embodiments, the management server 522 does not communicate directly with the medical device 502, but receives information from the medical device 502 only through the collection server 504. In other embodiments, the management server 522 may be configured to communicate directly with the medical device 502.

The management server 522 may be configured to obtain information from the medical device 502, via the collection server 504, in any number of different ways. For example, the management server 522 may include a query component 526 configured to obtain indexed information 528 via a specific query (for example, a device-specific query). The query component 526 may be configured to query the database 520 in response to user input (received, for example, via the user device 524), automatically, according to a configured option, and/or the like. In embodiments, the collection server 504 may be configured to send indexed information 528 from the database 520 to the management server 522 according to a configured option such as, for example, anytime information is received by the collection server 504, periodically, anytime information associated with a failed self-test is received, and/or the like. To facilitate reliability, the management server 522 and/or the collection server 504 may be configured to provide an alert to the user device 524 in the event that information that is expected to be received about a particular medical device 502 is not received. This alert may be provided in the form of email, pop-up screens, and/or the like.

The management server 522 may include a device dashboard 530 that is configured to provide a graphical user interface (GUI) 532 with which a user can interact via the user device 524. The device dashboard 530 may be configured to interact with a database 534 to store, retrieve, and/or manipulate account information 536 associated with a particular user, user device, fleet of medical devices, and/or the like. In operation, for example, the user logs into the service provided by the device dashboard 530 using a username and password and is provided with information associated with medical devices 502 registered to that user. The device dashboard 530 may be configured to allow a customer to register medical devices, view a dashboard feature that presents overall compliance (for example, maintenance status of all registered medical devices), log maintenance checks, and view and edit information about medical devices and the sites in which they are located. In embodiments, the management server 522 provides a role-based system for device management corresponding to various sites at which the medical devices are located.

As is further shown in FIG. 5, the illustrative operating environment 500 includes an integration component 538 that is configured to facilitate interaction between the database 520 and one or more systems or devices. For example, as shown, the integration component 538 may be configured to provide indexed information (for example, clinical event information) 528 to an electronic medical record (EMR) system 540, an administration system 542, and/or the like. The EMR system 540 may be any EMR system, combination of EMR systems and/or the like. In embodiments, the administration system 542 may be a system configured to administer one or more aspects of embodiments of the illustrative operating environment 500. For example, the administration system 542 may be associated with an entity that manages, hosts, and/or otherwise provides the management server 522, the collection server 504, the medical device 502, and/or the like. Embodiments of the administration system 542 may facilitate quality control, software updates, configuration updates, legal compliance, and/or the like.

The illustrative operating environment 500 shown in FIG. 5 is not intended to suggest any limitation as to the scope of use or functionality of embodiments of the present invention. Neither should the illustrative operating environment 500 be interpreted as having any dependency or requirement related to any single component or combination of components illustrated therein. Additionally, any one or more of the components depicted in FIG. 5 may be, in embodiments, integrated with various ones of the other components depicted therein (and/or components not illustrated), all of which are considered to be within the ambit of the present invention.

Certain embodiments of the present disclosure may be described with reference to various non-limiting examples.

Example 1

A medical device 304, such as an AED, is mounted on the wall at a location, for example an office building. The AED includes one or more batteries 312 and one or more patient interface components 314, for example electrodes. The AED runs a self-test to assess its device readiness, for example by determining whether the battery 312 is operational and/or is carrying a sufficient charge to operate in an emergency medical event. The AED self-test may also determine whether the electrodes 314 are functioning and/or whether they need to be replaced, for example if continuity has been disrupted or if the AED notes the passage of a certain period of time since the installation of the electrodes 314 indicating their expiration or near expiration. Various other or additional device readiness information may be observed by the AED and/or stored in a memory, for example memory 320. The AED 304 may be communicably coupled to the network 306 by a WiFi connection. After the self-test, and/or according to a schedule, the AED 304 sends or transfers device readiness information to the server 302 via the network 306. In some cases, sending or transfer of device readiness information occurs automatically, and/or with or without a request or query made by or originating with the server 302. In other cases, the user of the AED makes a selection on the AED 304 to push the device readiness information to the server 302. If a fault or device readiness error or condition is present in the message from the AED 304 to the server 302, the server 302 may automatically notify a user, for example by initiating a visual and/or audio message on the user device 310, according to embodiments of the present disclosure.

In this example embodiment, these steps may be carried out according to the left side of the flow diagram of FIG. 4. It should be noted that blocks 402, 404, 406, 408, and 410 of the left side may occur independently of blocks 418, 420, 422, 424, and 426 of the right side and that some devices may include the functionality of the left side of this diagram, some of the right side of this diagram, and some of both sides of this diagram.

Example 2

A medical device 304, such as an AED, is mounted on the wall at a location, for example an office building. The AED runs a self-test to assess its device performance, for example by determining whether the software of the AED is running correctly and without faults and/or whether the AED itself is in working condition or functioning internally. Various other or additional device performance information may be observed by the AED and/or stored in a memory, for example memory 320. The AED 304 may be communicably coupled to the network 306 by a WiFi connection. After the self-test, and/or according to a schedule, the AED 304 sends or transfers device performance information to the server 302 via the network 306. In some cases, sending or transfer of device performance information occurs automatically, and/or with or without a request or query made by or originating with the server 302. In other cases, the user of the AED makes a selection on the AED 304 to push the device performance information to the server 302. If a fault or device performance error or condition is present in the message from the AED 304 to the server 302, the server 302 may automatically notify a user, for example by initiating a visual and/or audio message on the user device 310, according to embodiments of the present disclosure.

In this example embodiment, these steps may be carried out according to the left side of the flow diagram of FIG. 4, where device performance is assessed or observed instead of or in addition to the various device readiness information discussed above, according to embodiments of the present disclosure.

Example 3

A medical device 304, such as an AED, is mounted on the wall at a location, for example an office building. During a medical event, such as a medical emergency, the AED is de-mounted and used on a patient during the medical emergency. De-mounting and/or using the AED on a patient may involve activating or selecting a "therapy mode" on the AED, which may be distinguished from a standby mode or other mode in which the AED operates for the long periods of time when it is mounted on the wall (or other location). During the medical emergency, the AED gathers and stores clinical event information. The AED 304 may be communicably coupled to the network 306 by a WiFi connection. After the clinical event, the AED is configured to send or transfer the clinical event information to the server 302 via the network 306. In some cases, the sending or transfer of clinical event information occurs automatically, and/or with or without a request or query made by or originating with the server 302. In other cases, the user of the AED makes a selection on the AED 304 to push the clinical event information to the server 302.

In this example embodiment, these steps may be carried out according to the right side of the flow diagram of FIG. 4, according to embodiments of the present disclosure.

Example 4

A medical device 304, such as an AED, is mounted on the wall at a location, for example an office building. The AED may be one of a number of device types, and/or may be running one of a number of different software versions. Either in response to an AED administrative user request and/or automatically, the AED 304 sends a message to the server 302 indicating the AED device type and/or serial number and/or current software version, and the configuration component 348 and/or update component 352 of the server 302 sends a software or configuration update to the AED 304 corresponding to the device and/or needed software version. According to such configurations of communication component 316 of the AED 304, there is no need for multiple back-and-forth messages in order to initiate a device or component update, according to embodiments of the present disclosure. In certain embodiments, the server 302 may automatically send software or configuration updates to the AED 304.

According to some embodiments, a user logs into a user device 310 and requests software or configuration updates for all devices 304, 308 managed by the user or customer. According to other embodiments, the devices 304, 308 automatically update their software or configurations via their respective WiFi connections.

Embodiments of the present disclosure include systems and methods having one or more features of any or all combinations of the features described above with respect to Examples 1 to 4, as well as the other examples and embodiments discussed herein. For example, an AED 304 may be configured to transmit, either via a user push and/or an automatic push, to the server 302 one or more of clinical event information, device readiness information, and device performance information. This may be done simultaneously, according to some embodiments. According to some embodiments, software or configuration upgrades are requested manually or otherwise by a user, either via the AED 304 and/or the server 302; according to other embodiments, software or configuration upgrades are requested automatically. In certain embodiments, the medical device or server may transmit, push or pull, automatically or manually, one or more of clinical event information, device readiness information, device performance information, configuration updates and/or software updates. Communication between the device and server may be unidirectional or bidirectional.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. A medical device system for use in patient resuscitation and medical device management, the medical device system comprising:
    a fleet of medical devices associated with a common administrator and distributed over multiple locations, each medical device comprising:
        a first memory,
        a first processor communicably coupled to the first memory and configured to store a medical device information comprising:
            a device status information comprising device-readiness information from a medical device self-test, and
            a clinical event information observed by the medical device during a use of the medical device during a clinical event, the clinical event information comprising a CPR performance data received by the medical device from a CPR chest compression sensor, and
        a first communication component communicably coupled to the first processor and configured to transmit the stored medical device information via a network,
        wherein the at least one medical device comprises one or more of an external defibrillator, an automated external defibrillator, and a compression assistance device; and
    one or more servers communicatively coupled to the fleet of medical devices and configured to provide a guided user interface (GUI) for the common administrator at a display of a user device located remotely from the multiple locations, the one or more servers comprising:
        a second communication component configured to receive the medical device information transmitted from the fleet of medical devices by each first communication component,
        a second memory configured to store the received medical device information, and
        a second processor configured to execute a device dashboard service configured to provide, at the GUI, a report for the fleet of medical devices comprising the device-readiness information for the fleet of medical devices.

2. The medical device system of claim 1, wherein the first communication component is configured to wirelessly transmit some or all of the medical device information automatically when the medical device satisfies a predetermined condition of operation.

3. The medical device system of claim 2, wherein the predetermined condition of operation is that power to the medical device is turned off.

4. The medical device system of claim 2, wherein the predetermined condition of operation is that the medical device is connected to a power charging dock.

5. The medical device system of claim 2, wherein the predetermined condition of operation is a termination of the clinical event.

6. The medical device system of claim 2, wherein the predetermined condition of operation is a self-test.

7. The medical device system of claim 1, wherein the first communication component comprises a WiFi interface.

8. The medical device system of claim 1, wherein the first communication component is configured to transmit the medical device information via a computer network, a cellular network, or a combination thereof.

9. The medical device system of claim 1, wherein the clinical event information comprises one or more of device prompting records, device actions, device operations, faults, and errors.

10. The medical device system of claim 1, wherein the device-readiness information comprises one or more of battery status information, battery condition information, and self-test information.

11. The medical device system of claim 1, wherein the user device comprises a laptop computer, a tablet computer, or a hand-held device.

12. The medical device system of claim 1, wherein the GUI provides device status alerts.

13. The medical device system of claim 1, wherein the one or more servers enable the user device to provide event logs and device prompt logs from the clinical event information.

14. The medical device system of claim 1, wherein the one or more servers enable the user device to provide waveform data comprising one or more of ECG, blood oxygen level, and end-tidal carbon dioxide.

15. The medical device system of claim 1, wherein the one or more servers enable the user device to provide one or more of CPR analysis and CPR quality prompts from the clinical event information.

16. The medical device system of claim 1, wherein the one or more servers enable the user device to provide a customer registration wizard configured to walk the common administrator through a medical device registration process for the fleet of medical devices, wherein the fleet of medical devices is associated with account information accessible by the one or more servers.

17. The medical device system of claim 1, wherein the one or more servers enable the user device to remotely access audio and/or video equipment associated with the fleet of medical devices.

18. The medical device system of claim 1,
wherein the medical device information comprises device performance information, and
wherein the one or more servers enable the user device to provide the device performance information.

19. The medical device system of claim 18, wherein the device performance information comprises a number of times a defibrillation shock was applied during the clinical event and an energy level of the applied defibrillation shock.

20. The medical device system of claim 1, wherein the one or more servers are configured to implement a software-as-a-service (SaaS) cloud data collection platform.

21. The medical device system of claim 1, wherein the one or more servers are configured to provide the clinical event information to an electronic medical record system.

22. The medical device system of claim 1, wherein the report is a statistical report for the fleet of medical devices comprising statistics for the medical device information.

23. The medical device system of claim 22, wherein the statistical report for the fleet of medical devices comprises statistical reports across at least one of geographic areas, customers, medical devices within the fleet of medical devices, device types, devices of certain ages, device versions, device configurations, device environmental conditions, device use conditions, device user demographics, and patient outcomes.

24. The medical device system of claim 22, wherein the device dashboard service is configured to periodically generate the report automatically.

25. The medical device system of claim 22, wherein the report is manually generated at the GUI by the common administrator.

26. The medical device system of claim 1, wherein the multiple locations comprise at least one of multiple geographic locations, multiple locations associated with a customer, and multiple locations within an individual site.

* * * * *